(12) United States Patent
Eid

(10) Patent No.: US 10,945,638 B2
(45) Date of Patent: Mar. 16, 2021

(54) DISPOSABLE MEASURING TOOL

(71) Applicant: Coloplast A/S, Humlebaek (DK)

(72) Inventor: J. Francois Eid, Larchmont, NY (US)

(73) Assignee: Coloplast A/S, Humlebaek (DK)

(*) Notice: Subject to any disclaimer, the term of this patent is extended or adjusted under 35 U.S.C. 154(b) by 356 days.

(21) Appl. No.: 15/298,892

(22) Filed: Oct. 20, 2016

(65) Prior Publication Data
US 2017/0105657 A1    Apr. 20, 2017

Related U.S. Application Data

(60) Provisional application No. 62/243,911, filed on Oct. 20, 2015.

(51) Int. Cl.
| | | |
|---|---|---|
| *A61B 5/107* | (2006.01) | |
| *A61B 5/00* | (2006.01) | |
| *A61F 2/26* | (2006.01) | |
| *A61B 90/00* | (2016.01) | |
| *A61B 17/00* | (2006.01) | |

(52) U.S. Cl.
CPC .......... *A61B 5/1071* (2013.01); *A61B 5/1073* (2013.01); *A61B 5/1076* (2013.01); *A61B 5/6847* (2013.01); *A61F 2/26* (2013.01); *A61B 5/4393* (2013.01); *A61B 2017/0023* (2013.01); *A61B 2090/061* (2016.02); *A61B 2090/067* (2016.02); *A61B 2505/05* (2013.01); *A61B 2562/164* (2013.01)

(58) Field of Classification Search
CPC ........ A61B 5/107; A61B 5/1071–1073; A61B 5/1076; A61B 5/6847; A61B 2017/320044; A61B 2017/320048; A61B 2017/320056; A61F 2/26; A61M 29/00; G01B 21/00; G01B 21/02; G01B 3/30; G01B 5/18; G01B 3/02; G01B 3/004
USPC .................................................... 33/669, 700
See application file for complete search history.

(56) References Cited

U.S. PATENT DOCUMENTS

| | | | | |
|---|---|---|---|---|
| 1,677,387 A | | 7/1928 | Gaidos | |
| 4,594,998 A | * | 6/1986 | Porter | A61F 2/26 600/40 |
| 5,968,067 A | * | 10/1999 | Mooreville | A61F 2/26 600/40 |
| 6,010,520 A | * | 1/2000 | Pattison | A61M 29/00 606/191 |

(Continued)

FOREIGN PATENT DOCUMENTS

| | | |
|---|---|---|
| CN | 201668856 U | 12/2010 |
| WO | 2004045421 A1 | 6/2004 |
| WO | 2011079847 A1 | 7/2011 |

OTHER PUBLICATIONS

Bazic, Bazic 12-inch (30cm) Shatterproof Flexible Ruler Case of 24, Nov. 15, 2012 (from customer reviews), Amazon. https://www.amazon.com/BAZIC-12-Inch-Shatterproof-Flexible-Ruler/dp/B00A4C9GXQ/ref=sr_1_5?s=office-products&ie=UTF8&qid=1550068950&sr=1-5&keywords=flexible%2Bruler&th=1 (Year: 2012).*

*Primary Examiner* — Daniel L Cerioni
*Assistant Examiner* — Raymond P Dulman
(74) *Attorney, Agent, or Firm* — Coloplast Corp., Coloplast A/S; Nick Baumann

(57) ABSTRACT

A disposable measuring tool is disclosed for used during the implantation of a penile prosthesis cylinder. The measuring tool permits an accurate measurement of a dilated corpus cavernosum prepared to accept and penile prosthesis cylinder.

8 Claims, 4 Drawing Sheets

(56) References Cited

U.S. PATENT DOCUMENTS

| | | | |
|---|---|---|---|
| 6,450,977 B1 * | 9/2002 | Baxter-Jones | A61B 5/1076 600/591 |
| 6,613,002 B1 * | 9/2003 | Clark | A61B 5/1076 600/104 |
| 7,985,176 B1 * | 7/2011 | Morningstar | A61F 2/26 600/40 |
| 9,126,018 B1 * | 9/2015 | Garrison | A61B 17/0218 |
| 2004/0225182 A1 * | 11/2004 | Eid | A61F 2/26 600/38 |
| 2007/0151116 A1 * | 7/2007 | Malandain | A61B 1/3135 33/512 |
| 2010/0010530 A1 | 1/2010 | Rhee | |
| 2010/0228267 A1 * | 9/2010 | Mercado | A61B 5/1076 606/131 |
| 2011/0054250 A1 | 3/2011 | Morningstar | |
| 2014/0276234 A1 * | 9/2014 | Hines | A61B 5/1076 600/591 |
| 2016/0270695 A1 * | 9/2016 | Trokel | A61B 5/1072 |

* cited by examiner

DISPOSABLE MEASURING TOOL

CROSS REFERENCE TO RELATED APPLICATIONS

This application claims benefit under 35 U.S.C. § 119(e) to U.S. Ser. No. 62/243,911, filed Oct. 20, 2015, the contents of both of which are incorporated herein by reference in their entirety.

FIELD OF THE INVENTION

The invention relates generally to a disposable measuring tool for use during the implantation of inflatable penile prosthesis cylinders.

BACKGROUND OF THE INVENTION

Penile prosthesis is one of the oldest and most effective treatments for the condition of erectile dysfunction. A penile prosthesis typically includes inflatable or non-inflatable cylinders that are implanted into the corpora cavernosa of the penis.

Implantation of a penile prosthesis is an invasive treatment that requires a delicate and often painful implant to install. Simplification of surgical procedures and minimization of time in the operation has many beneficial implications. To reach a corpora cavernosum of the penis and implant the cylinders, the surgeon will first make an incision at the base of the penis, such as where it meets the scrotum. The patient is prepared for the cylinder after the surgeon has dilated each corpora cavernosum to create space for the cylinders. A surgical tool such as a Furlow or Dilamezinsert are often used to measure the volume of the dilated space to allow the surgeon to select a cylinder of appropriate dimensions. Current tools employed for this purpose are thinner than the actual cylinder at the distal end to be implanted, thus overestimating the distal measurement. On the other hand, the current tools are thicker than the actual cylinder at the proximal end, thus underestimating the proximal measurement. Implanting an inflatable cylinder that does not match the size of the patent's corpora cavernosum requires resizing the cylinders. Having to resize the cylinders by adding or eliminating rear tip extenders can cause many unnecessary complications, such as increased operation time, greater contact of the cylinders with the patients skin, and the potential of the traction suture which has come into contact with the foley catheter to be dragged inside the sterile corporal body, all of which increase the possibility of infection.

Currently, there is no such device that is the same size and shape of penile prosthesis cylinders available to correctly measure the length of the corpora. This disclosure discloses various embodiments of disposable and easily sterilizable tools to accurately measure the size of the inflatable penile implant cylinder needed.

BRIEF SUMMARY OF THE INVENTION

Presently, there is no tool to perform adequate measurement of the proximal and distal portion of the interior of the penis. Instead, surgeons have been using a Furlow or Dilamezinsert to measure the corpora. Both of these instruments are narrower than the cylinders at the distal end and wider than the cylinders at the proximal end. This leads to an imprecise measurement and often surgeons must add or subtract a centimeter from the measurement obtained in order to adequately place the implant.

The present invention provides a disposable measuring tool including a distal portion, a proximal portion, and a body portion disposed therebetween. The body portion has a first diameter. The distal portion has a second diameter less than the first diameter. The proximal portion has a third diameter less than the first diameter of the body portion. The disposable measuring tool has a measuring surface on the surface of the body portion, wherein the first diameter decreases to the distal end and proximal end, and wherein the disposable measuring tool is used to measure the corpus cavernosum of a patient receiving a penile prosthesis cylinder.

According to one embodiment of the disclosure, a disposable measuring tool includes a proximal portion having a proximal diameter; a distal portion having a distal diameter; a body portion having a body diameter, wherein the body portion is disposed between the proximal portion and the distal portion, the body diameter is larger than the proximal diameter and the distal diameter; the body portion is tapered from a midline of the body portion toward both the proximal portion and the distal portion; and a measuring surface disposed on the body portion. The measuring surface further includes a proximal marking, the proximal marking being configured to be read uprightly when a proximal end of the disposable measuring tool is inserted into a proximal end of a corpus cavernosum. And, the measuring surface further includes a distal marking, the distal marking being configured to be read uprightly when a distal end of the disposable measuring tool is inserted into a distal end of the corpus cavernosum, wherein the proximal marking and the distal marking are arranged in opposite directions.

According to another embodiment of the disclosure, a disposable measuring tool includes a proximal portion having a proximal diameter; a distal portion having a distal diameter; a body portion having a body diameter, wherein the body portion is disposed between the proximal portion and the distal portion, the proximal portion is connected to the body portion with an angle $\alpha$, the body diameter is larger than the proximal diameter and the distal diameter; the body portion is tapered from a midline of the body portion toward both the proximal portion and the distal portion; and a measuring surface disposed on the body portion. The measuring surface further includes a proximal marking, the proximal marking being configured to be read uprightly when a proximal end of the disposable measuring tool is inserted into a proximal end of a corpus cavernosum. And, the measuring surface further includes a distal marking, the distal marking being configured to be read uprightly when a distal end of the disposable measuring tool is inserted into a distal end of the corpus cavernosum, wherein the proximal marking and the distal marking are arranged in opposite directions.

According to another embodiment of the disclosure, a surgical method using a disposable measuring tool includes accessing a corpus cavernosum of a penis of a patient; dilating the corpus cavernosum; inserting a distal end of a disposable measuring tool into the corpus cavernosum toward a distal end of the corpus cavernosum; measuring a distal length of the corpus cavernosum using the disposable measuring tool; inserting a proximal end of the disposable measuring tool into the corpus cavernosum toward a proximal end of the corpus cavernosum; measuring a proximal length of the corpus cavernosum using the disposable measuring tool; and selecting an inflatable penile implant cylinder according to a sum of the distal length and the proximal length of the corpus cavernosum.

The following includes definitions of various terms and phrases used throughout this specification.

The term "reading uprightly" means reading the text, number, or symbol from left to right by a person with his head in an upright position.

The terms "about" or "approximately" are defined as being close to as understood by one of ordinary skill in the art, and in one non-limiting embodiment the terms are defined to be within 10%, preferably within 5%, more preferably within 1%, and most preferably within 0.5%.

The term "substantially" and its variations are defined as being largely but not necessarily wholly what is specified as understood by one of ordinary skill in the art, and in one non-limiting embodiment substantially refers to ranges within 10%, within 5%, within 1%, or within 0.5%.

The terms "inhibiting" or "reducing" or "preventing" or "avoiding" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The methods of the present invention can "comprise," "consist essentially of," or "consist of" particular ingredients, components, compositions, etc. disclosed throughout the specification. With respect to the transitional phase "consisting essentially of," in one non-limiting aspect, a basic and novel characteristic of the methods is the ability to efficiently implant penile prosthesis cylinders.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DETAILED DESCRIPTION

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

These and other non-limiting aspects of the present invention are discussed in further detail in the following paragraphs.

There is no such device that is the same size and shape of penile prosthesis cylinders available to correctly measure the length of the corpora. This disclosure discloses various embodiments of disposable and easily sterilizable tools to accurately measure the size of the inflatable penile implant cylinder needed.

The disposable measuring tool disclosed herein addresses issues to accurately measure where the cylinder tip is to be place in the corpora of the penis and allow the surgeon to reconcile this measurement with proximal and distal measurements of penile length. The disclosed tool is useful for the success and patient satisfaction with the implant by alleviating potential problems, such as the need for resizing the penile implant and the increased possibility of infection associated thereof.

The present disclosure provides a disposable measuring tool for use during implantation of penile prosthesis cylinders. It is envisioned without limitation, that the tools and methods disclosed herein can be used for the implantation of Coloplast's male urology products including, for example, Titan®, Genesis®, Alpha I®, Excel™, and Mark II® penile implants for the treatment of erectile dysfunction. It is also envisioned that the tools and methods disclosed herein can be used for the implantation of other brands of penile prosthetics including Promedon-Tube® (Cordoba, Argentina); Silimed® prosthesis (Rio de Janerio, Brazil); Jonas® prosthesis by Bard Co. (Murray Hill, N.J., USA); Virilis I™ and Virilis II™ prostheses by Giant Medical (Cremona, Italy); Apollo™ prosthesis by Giant Medical Corporation (Cremona, Italy); AMS 600™, AMS 650T™, Dura II™, Ambicor®, and AMS 700T™ series 700 CX, Ultrex, and CXR by American Medical Systems (Minnetonka, Minn., USA). Both inflatable and non-inflatable semirigid penile implants are envisioned in the current embodiments.

Figure 1:
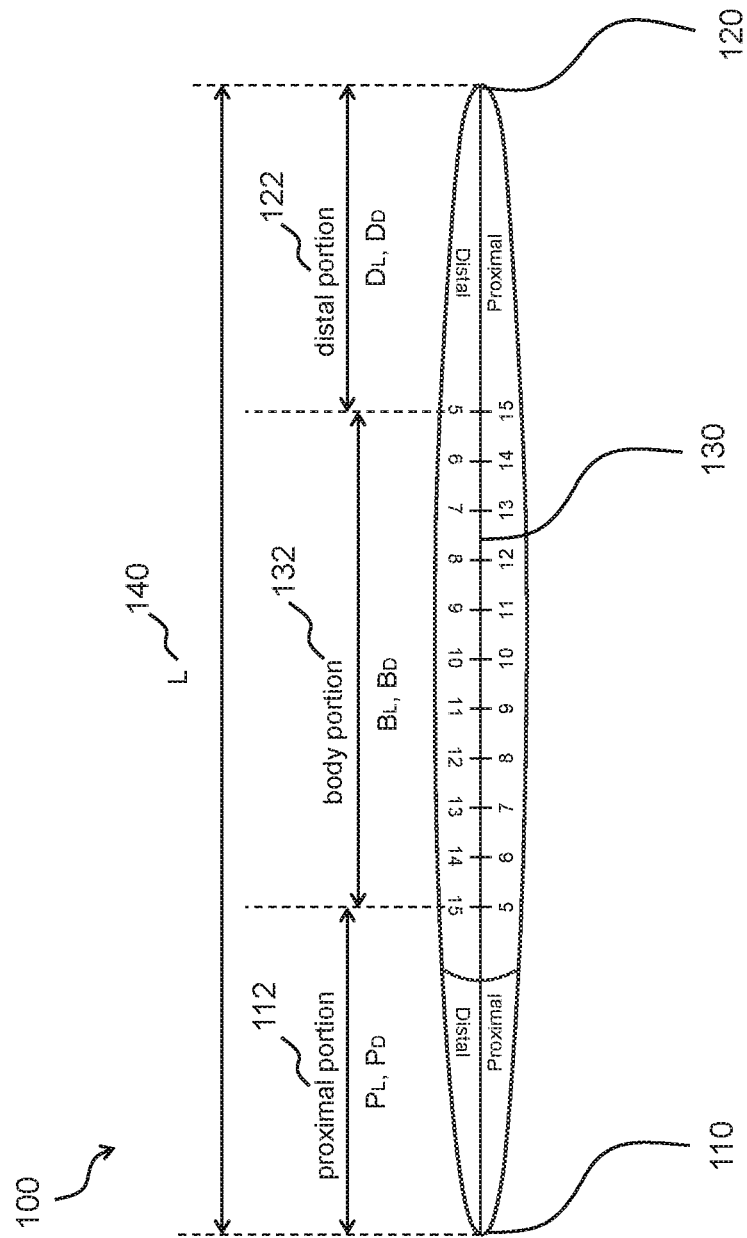
FIG. 1 is a drawing of a disposable measuring tool according to one embodiment of the disclosure.

FIG. 1 is a drawing of the disposable measuring tool 100 according to one embodiment of the disclosure. The disposable measuring tool 100 can include all the features of the disposable measuring tool 200 in FIG. 2. The disposable measuring tool 100 can include all the features of the disposable measuring tool 300 in FIG. 3. The disposable measuring tool 100 can be used in the surgical method 400 in FIG. 4.

As shown in FIG. 1, disposable measuring tool 100 of the current invention comprises a hollow, solid, or semisolid material having distal end 120 and proximal end 110. The disposable measuring tool 100 has a proximal portion 112 with a proximal length PL and a proximal diameter PD. The disposable measuring tool 100 has a distal portion 122 with a distal length DL and a distal diameter DD. The disposable measuring tool 100 has a body portion 132 with a body length BL and a body diameter BD. The body portion 132 is disposed between the proximal portion 112 and the distal portion 122. The disposable measuring tool 100 has a total length L 140.

Disposable measuring tool 100 is shaped appropriately for insertion into the patient to mimic the morphology of each corpora. Disposable measuring tool 100 may be straight or slightly conformed. In one instance, disposable measuring tool 100 can be slightly angled at distal end 120 so that when inserted it directs towards the urinary meatus. In another instance, disposable measuring tool 100 can also be slightly angled at proximal end 110 to follow the curvature of the corpora towards the attachment point on the pubic ramus. Specifically, disposable measuring tool 100 may have a gentle 5 to 30 degree turn at about ⅓ from the proximal end.

As shown in FIG. 1, the disposable measuring tool 100 has a line 130 which runs on the midline along its entire length and is etched or marked with numbers and/or grooves every millimeter separately indicating centimeters starting at 5 cm from proximal end 110 and ending at 15 cm or more at distal end 120. On the other side of the midline 130, numbers and grooves are etched or marked in the opposite direction starting at 5 cm from the tip of distal end 120 and ending at 15 cm or more on the tip of proximal end 110.

The measuring surface of the tool can have the appearance of a ruler or any measurement indicator that is easily identified by the surgeon under operation conditions. The measuring surface can be disposed on one side, e.g., front side or back side, of the disposable measuring tool 100. In alternative, the measuring surface can be disposed on opposite sides of the disposable measuring tool 100, e.g., front and back sides.

Specifically, disposable measuring tool 100 is marked with the words "DISTAL" on one side of the midline 130 and "PROXIMAL" on the other side of the midline 130 as shown in FIG. 1. The markings of "PROXIMAL" in both proximal portion 112 and distal portion 122 are configured to coordinate with the proximal measurement centimeter/millimeter markings such that when the proximal end 110 is inserted into the proximal end of the patient's penis, the proximal measurement can be read uprightly. The markings of "DISTAL" in both proximal portion 112 and distal portion 122 are configured to coordinate with the distal measurement centimeter/millimeter markings such that when the distal end 120 is inserted into the distal end of the patient's penis, the distal measurement can be read uprightly.

As shown in FIG. 1, assuming a patient's penis position does not change during a surgery, a surgeon may need to change his standing position in order to read the distal markings and proximal markings uprightly. For example, as shown in FIG. 1, with a standing position, the surgeon may read the proximal markings uprightly when a proximal end of the disposable measuring tool is inserted into a proximal end of a corpora cavernosa; however, the surgeon may need to change his standing position 180 degree (e.g., across the surgery table) to read the distal markings uprightly when a distal end of the disposable measuring tool is inserted into a distal end of the corpora cavernosa, assuming the penis position does not change. It is noted, as the embodiment shown in FIG. 1, the proximal markings and the distal markings can be read uprightly by two persons facing each other, e.g., a surgeon and an assistant standing across the surgery table facing each other.

Or alternatively, in another embodiment, a design of the disposable measuring tool may have distal and proximal markings separately on opposite sides (front and back) of the disposable measuring tool 100, such that the surgeon can read both the distal markings and proximal markings uprightly by flipping the disposable measuring tool without changing his standing position. For example, the proximal markings are disposed on a front side of the disposable measuring tool, and the distal markings are disposed on a back side of the disposable measuring tool. In such front-and-back configuration, the surgeon can read the proximal markings on the front side uprightly when a proximal end of the disposable measuring tool is inserted into a proximal end of a corpora cavernosa. And yet, by merely flipping the disposable measuring tool to the back side, the surgeon can read the distal markings uprightly when a distal end of the disposable measuring tool is inserted into a distal end of the corpora cavernosa, while the penis position and the surgeon's standing position both stay still.

The disposable measuring tool 100 may have any other literal means that would allow the surgeon to easily identify which side of the midline is being observed.

In one embodiment, disposable measuring tool 100 would be available in different sizes and measurements depending on the type of cylinders being implanted. The disposable measuring tool 100 can have total length L 140 that ranges from about 10 cm to about 30 cm or any length therebetween including about 11 cm, about 12 cm, about 13 cm, about 14 cm, about 15 cm, about 16 cm, about 17 cm, about 18 cm, about 19 cm, about 20 cm, about 21 cm, about 22 cm, or about 23 cm, about 24 cm, about 25 cm, about 26 cm, about 27 cm, about 28 cm, or about 29 cm. In one instance, the distal measurement surface of the disposable measuring tool 100 may have a length up to 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, or 25 cm. The proximal measurement surface of the disposable measuring tool 100 may have a length up to 6 cm, 7 cm, 8 cm, 9 cm, 10 cm, 11 cm, 12 cm, 13 cm, 14 cm, 15 cm, 16 cm, 17 cm, 18 cm, 19 cm, 20 cm, 21 cm, 22 cm, 23 cm, 24 cm, or 25 cm.

The disposable measuring tool 100 can have distal portion 122 length DL that ranges from about 1 cm to about 15 cm or any length therebetween including about 1 cm, about 2 cm, about 3 cm, about 4 cm, about 5 cm, about 6 cm, about 7 cm, about 8 cm, about 9 cm, about 10 cm, about 11 cm, about 12 cm, or about 13 cm, about 14 cm, or about 15 cm.

The disposable measuring tool 100 can have proximal portion 112 length PL that ranges from about 1 cm to about 15 cm or any length therebetween including about 1 cm, about 2 cm, about 3 cm, about 4 cm, about 5 cm, about 6 cm, about 7 cm, about 8 cm, about 9 cm, about 10 cm, about 11 cm, about 12 cm, or about 13 cm, about 14 cm, or about 15 cm.

The disposable measuring tool 100 can have body portion 132 length BL that ranges from about 1 cm to about 15 cm or any length therebetween including about 1 cm, about 2 cm, about 3 cm, about 4 cm, about 5 cm, about 6 cm, about 7 cm, about 8 cm, about 9 cm, about 10 cm, about 11 cm, about 12 cm, or about 13 cm, about 14 cm, or about 15 cm.

In a specified instance, the distal measurement surface of the disposable measuring tool 100 may have a length up to 15 cm and the proximal measurement surface of the disposable measuring tool 100 may have a length up to 6 cm when performing the surgery through the scrotum, but could be much longer when measuring through an infrapubic approach. In this instance, the disposable measuring tool 100 would have an overall physical length of 22 to 24 cm to allow easy handling of the disposable measuring tool 100 when measuring larger corpora. A specific tool envisioned would be used to measure penises of 12 to 28 cm in total length.

The disposable measuring tool 100 can have a body diameter BD of the body portion 132 that ranges from about 1 cm to about 3 cm or any diameter therebetween including about 1.1 cm, about 1.2 cm, about 1.3 cm, about 1.4 cm, about 1.5 cm, about 1.6 cm, about 1.7 cm, about 1.8 cm, about 1.9 cm, about 2 cm, about 2.1 cm, about 2.2 cm, about 2.3 cm, about 2.4 cm, about 2.5 cm, about 2.6 cm, about 2.7 cm, about 2.8 cm, or about 2.9 cm.

The disposable measuring tool 100 can have a distal diameter DD of the distal portion 122 that ranges from about 0.5 cm to about 3 cm or any diameter therebetween including about 0.5 cm, about 0.6 cm, about 0.7 cm, about 0.8 cm, about 0.9 cm, about 1.0 cm, about 1.1 cm, about 1.2 cm, about 1.3 cm, about 1.4 cm, about 1.5 cm, about 1.6 cm, about 1.7 cm, about 1.8 cm, about 1.9 cm, about 2 cm, about 2.1 cm, about 2.2 cm, about 2.3 cm, about 2.4 cm, about 2.5 cm, about 2.6 cm, about 2.7 cm, about 2.8 cm, or about 2.9 cm.

The disposable measuring tool 100 can have a proximal diameter PD of the proximal portion 112 that ranges from about 0.5 cm to about 3 cm or any diameter therebetween including about 0.5 cm, about 0.6 cm, about 0.7 cm, about 0.8 cm, about 0.9 cm, about 1.0 cm, about 1.1 cm, about 1.2 cm, about 1.3 cm, about 1.4 cm, about 1.5 cm, about 1.6 cm, about 1.7 cm, about 1.8 cm, about 1.9 cm, about 2 cm, about 2.1 cm, about 2.2 cm, about 2.3 cm, about 2.4 cm, about 2.5 cm, about 2.6 cm, about 2.7 cm, about 2.8 cm, or about 2.9 cm.

In one embodiment, the maximum diameter of the body diameter BD is the first diameter. The first diameter is in the middle of the disposable measuring tool or slightly towards distal end 110 or proximal end 120. The diameter and circumference of the disposable measuring tool 100 decreases from the first diameter moving towards either distal end 120 or the proximal end 110 of the tool. The distal diameter DD has a second diameter less than the first diameter. The proximal diameter PD has a third diameter less than the first diameter of the body portion. This tapered shape moving from the first diameter towards either end of the tool can be symmetrical or unsymmetrical.

The tip of proximal end 110 shall not be too sharp to avoid proximal perforations. In one embodiment, the proximal end 110 can be configured to be more rounded to avoid perforations. In one embodiment, the proximal end 110 can be made with effectively soft materials, e.g., rubber, polyacrylate (acrylic, PMMA), etc, to avoid perforations.

The tip of distal end 120 shall not be too pointy to avoid distal perforations. In one embodiment, the distal end 120 can be configured to be more rounded to avoid perforations. In one embodiment, the distal end 120 can be made with soft effectively materials, e.g., rubber, polyacrylate (acrylic, PMMA), etc, to avoid perforations.

In some embodiments, disposable measuring tool 100 can be of identical to or of similar shape to the inflatable cylinder to be implanted at about 40% to about 100% inflated state. In one embodiment, the disposable measuring tool 100 is of identical to or of similar shape to the inflatable cylinder to be implanted at about 40%, 50%, 60%, 70%, 80%, 90%, or 100% inflated state.

Figure 2:
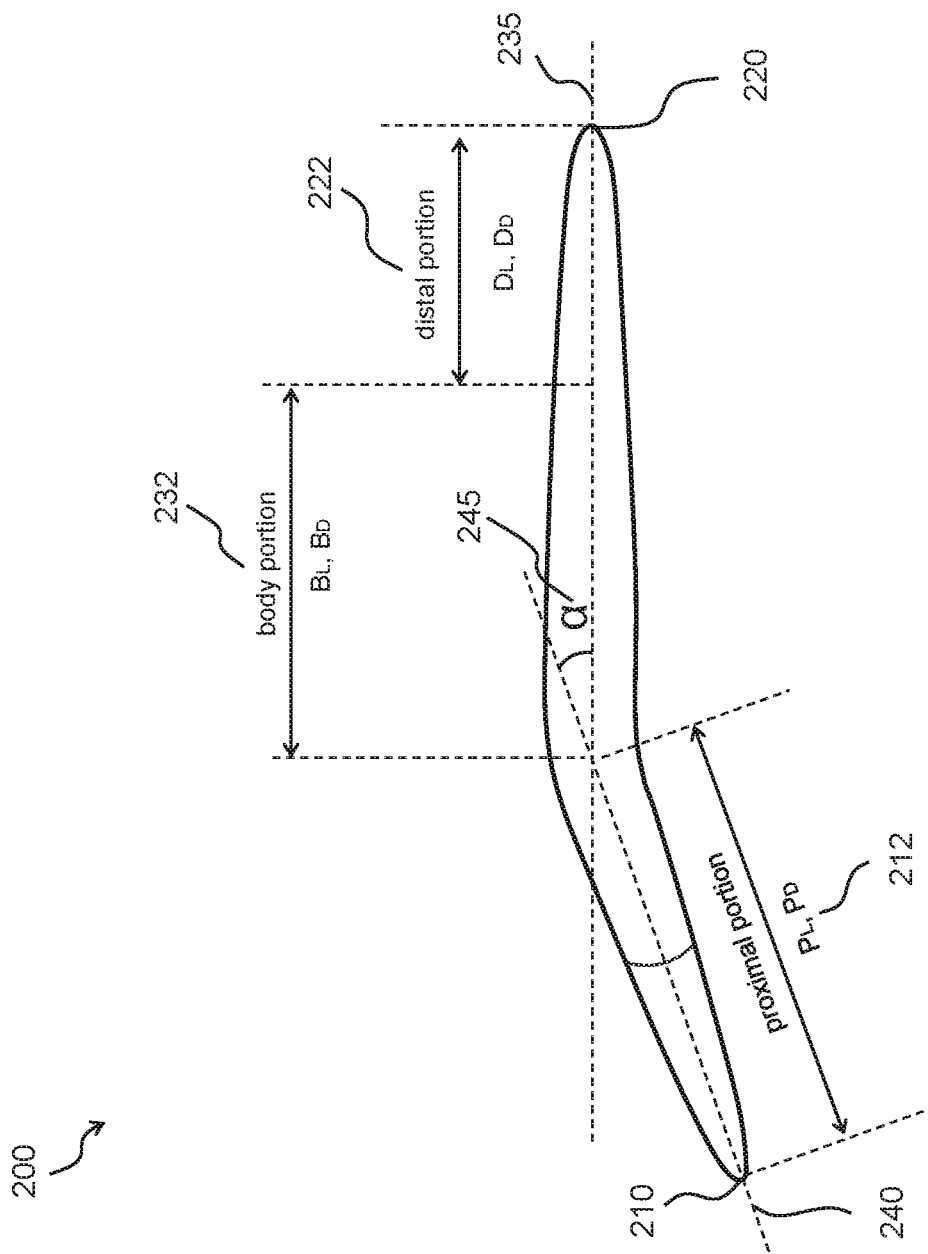
FIG. 2 is a drawing of a disposable measuring tool according to one embodiment of the disclosure.

FIG. 2 is a drawing of the disposable measuring tool 200 according to one embodiment of the disclosure. The disposable measuring tool 200 can include all the features of the disposable measuring tool 100 in FIG. 1. The disposable measuring tool 200 can include all the features of the disposable measuring tool 300 in FIG. 3. The disposable measuring tool 200 can be used in the surgical method 400 in FIG. 4.

As shown in FIG. 2, the disposable measuring tool 200 includes a proximal end 210 and a distal end 220. The disposable measuring tool 200 includes a proximal portion 212, a body portion 232, and a distal portion 222.

The disposable measuring tool 200 further includes a distal axis 235. The distal axis 235 is the longitudinal central axis 235 of the distal portion 222. The disposable measuring tool 200 further includes a proximal axis 240. The proximal axis 240 is the longitudinal central axis 235 of the proximal portion 212.

As shown in FIG. 2, the distal axis 235 intersects with the proximal axis 240 at an angle α 245. The angle α 245 ranges from about 5 degree to 35 degree. In one embodiment, the angle α 245 can be about 5 degree, about 10 degree, about 15 degree, about 20 degree, about 25 degree, about 30 degree, or about 35 degree.

As shown in FIG. 2, disposable measuring tool 200 is angled at proximal portion 212 to follow the curvature of the corpora towards the attachment point on the pubic ramus. Specifically, disposable measuring tool 200 may have a gentle 5 to 30 degree turn at about one third of the overall length from the proximal end 210. In one embodiment, PL (proximal length)=⅓ L (overall length of the disposable measuring tool).

In another embodiment, similar to the proximal portion being angled as shown in FIG. 2, disposable measuring tool 200 can also be angled at distal portion 222 so that when inserted into a penis, it directs towards the urinary meatus. The range of angles for the distal portion 222 may be the same as the angles for the proximal portion, e.g., from about 5 degree to 35 degree.

Figure 3:
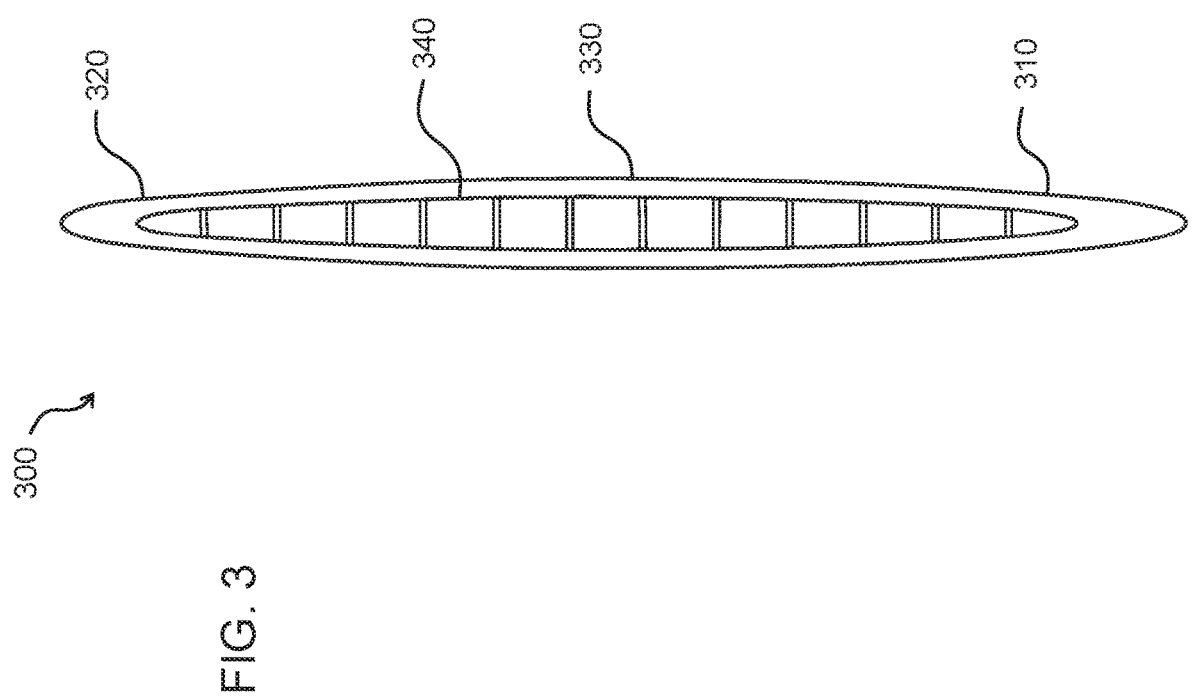
FIG. 3 is a drawing of a disposable measuring tool according to one embodiment of the disclosure.

FIG. 3 is a drawing of the disposable measuring tool 300 according to one embodiment of the disclosure. The disposable measuring tool 300 can include all the features of the disposable measuring tool 100 in FIG. 1. The disposable measuring tool 300 can include all the features of the disposable measuring tool 200 in FIG. 2. The disposable measuring tool 300 can be used in the surgical method 400 in FIG. 4.

As shown in FIG. 3, the disposable measuring tool 300 includes a proximal portion 310, a body portion 330, and a distal portion 320.

The disposable measuring tool 300 further includes a malleable mechanism 340 that allows the disposable measuring tool 300 to be malleable. In some examples, the corpora cavernosum needed to be measured is not straight, but curved in some manners. The malleability of the disposable measuring tool 300 provides the disposable measuring tool 300 the ability to adapt to the specific orientation of the individual corpora cavernosum for an accurate measurement.

The malleable mechanisms disclosed in U.S. Pat. Nos. 3,987,789, 4,392,562, 4,594,998, and 5,512,033 are hereby incorporated by reference. The malleable mechanisms disclosed in the cited references can be used to construct the malleable mechanism 340.

In one embodiment, disposable measuring tools 100, 200, 300 may include a hard or flexible polymer composition. Polymers used in medical applications that may be present in the disposable measuring tools 100, 200, 300 include polyethylene (PE), polypropylene (PP), polystyrene (PS), polyester (PET), polylactide (PLA), polycarbonate (PC), polyvinyl chloride (PVC), polyethersulfone (PES), polyacrylate (acrylic, PMMA), polysulfone (PSU), polyetheretherketone (PEEK), thermoplastic elastomers (TPE, TPU), thermoset elastomers (polysiloxane), poly-p-xylylene (Parylene), fluoropolymers (PTFE), or mixture thereof. In other aspects, disposable measuring tools 100, 200, 300 can be coated or encased in a soft and/or hypoallergenic material that can lessen abrasiveness or increase wettability for easier insertion and removal. In some aspects, disposable measuring tools 100, 200, 300 may also include natural polyisopene rubber (NR), synthetic polyisoprene rubber (IR), polybutadiene rubber (BR), chloropene rubber (CR), butyl rubber (IIR), halogenated butyl rubbers (CIIR, BIIR), styrene-butadiene rubber (SBR), nitrile rubber (NBR), hydrogenated nitrile rubber (HNBR), ethylene propylene rubber (EPM), ethylene propylene diene rubber (EPDM), epichlorohydrin rubber (ECO), polyacrylic rubber (ACM, ABR), silicone rubber (SI, Q, VMQ), fluorosilicone rubber (FSR, FVMQ), fluoroelastomers (FKM, FEPM), perfluoroelastomers (FFKM), polyether block amides (PEBA), chlorosulfonated polyethylene (CSM), ethylene-vinyl acetate (EVA), polyurethane (PU), polyethylene (PE), polypropylene (PP), polymethylmethacrylate (PMMA), melamine resin, or mixtures thereof.

In another embodiment, the disposable measuring tools 100, 200, 300 may comprise a surgical stainless steel which includes grades of stainless steel that are used in biomedical applications. The steels that may present in the disposable measuring tools 100, 200, 300 are austenitic stainless and martensitic and stainless steels. However the stainless steel can be any grade of corrosion resistant steel. Stainless steel, also referred to as "Marine Grade Stainless Steel", is a chromium, nickel, molybdenum alloy of steel that exhibits relatively good strength and corrosion resistance. Stainless steels, known also by the name "Cutlery Stainless Steel", are high carbon steels alloyed with chromium that have good corrosion resistance compared to other cutlery steels.

In other embodiments, the disposable measuring tools 100, 200, 300 may comprise at least chromium, nickel, or molybdenum, and combinations thereof. Other metals and alloys commonly used in medicine are gold (Au), cobalt-chrome alloys (CoCr), titanium and titanium alloys (TiNi, Ti—6Al—4V, Ti—Al—V, Ti—Al—Mo, Ti—Al—Cr, Ti—Al—Cr—Co, Ti—Al—Nb, Ti—Zr—Al) and silver-mercury alloys (AgHg). Titanium alloys may contain alpha stabilizers (aluminum, gallium, germanium, carbon, oxygen and nitrogen) or beta stabilizers (molybdenum, vanadium, tantalum, niobium, manganese, iron, chromium, cobalt, nickel, copper and silicon). Of the number of titanium alloys known, Ti—6Al—4V is most commonly employed, however Ti—6Al—6Nb shows even greater strength and resistance to corrosion.

In some embodiments, the disposable measuring tools 100, 200, 300 are disposable or easily sterilizable. It is envisioned that a disposable measuring tool 100, 200, 300 would comprise a inexpensive plastic material and an easily sterilizable material could be a material that bacteria adhere poorly too or are easily removed from, for example with detergents, disinfectants, or heat. Alternatively, an easily sterilizable material may be selected from any material that provides better resistance to bacterial colonization. Materials that are impregnated with antimicrobial agents are also envisioned in the current embodiments.

In other embodiments, the disposable measuring tools 100, 200, 300 have a hydrophilic coating to prevent bacteria adhesion and/or include one or more antibiotics depending on the preference of the surgeon. Any appropriate antibiotic may be employed that would treat bacteria generally associated with infection of penile prostheses. Specifically, the antibiotic of the current embodiments may have good efficacy against, but not limited to, *Escherichia coli, Escherichia klebsiella, Escherichia pseudomonas, Staphylococcus aureus, Staphylococcus epidermidis, Staphylococcus enterococcus faecalis*, and mixture thereof. Numerous antibiotics are available for use in the present embodiments, including but not limited to, Rifampicin, Streptomycin, Ciprofloxin, Vancomycin, Gentamicin, Flucloxacillin, and mixtures thereof. The antibiotic or antibiotics selected to be impregnated into the hydrophilic coating can be provided in liquid or powder form. It is also envisioned that a hydrophilic coating would increase wettability making insertion of the disposable measuring tool into the corpora easier.

Kits are also contemplated as being used in certain aspects of the invention. For instance, the disposable measuring tools 100, 200, 300 of the present invention can be included in a kit. A kit can include a container. Containers can include a case, sachet, pouch, package, compartment or other containers into which the surgical tool is retained. The kit can include indicia on its surface. The indicia, for example, can be a word, a phrase, an abbreviation, a picture, or a symbol. A kit can also include instructions for using the kit and the disposable measuring tools 100, 200, 300. A kit can include instructions that includes the surgical method 400 in FIG. 4.

Further, the disposable measuring tools 100, 200, 300 of the present invention may also be sterile, and the kits containing such tools can be used to preserve the sterility. The surgical tools may be sterilized via an aseptic manufacturing process or sterilized after packaging by methods known in the art.

Figure 4:
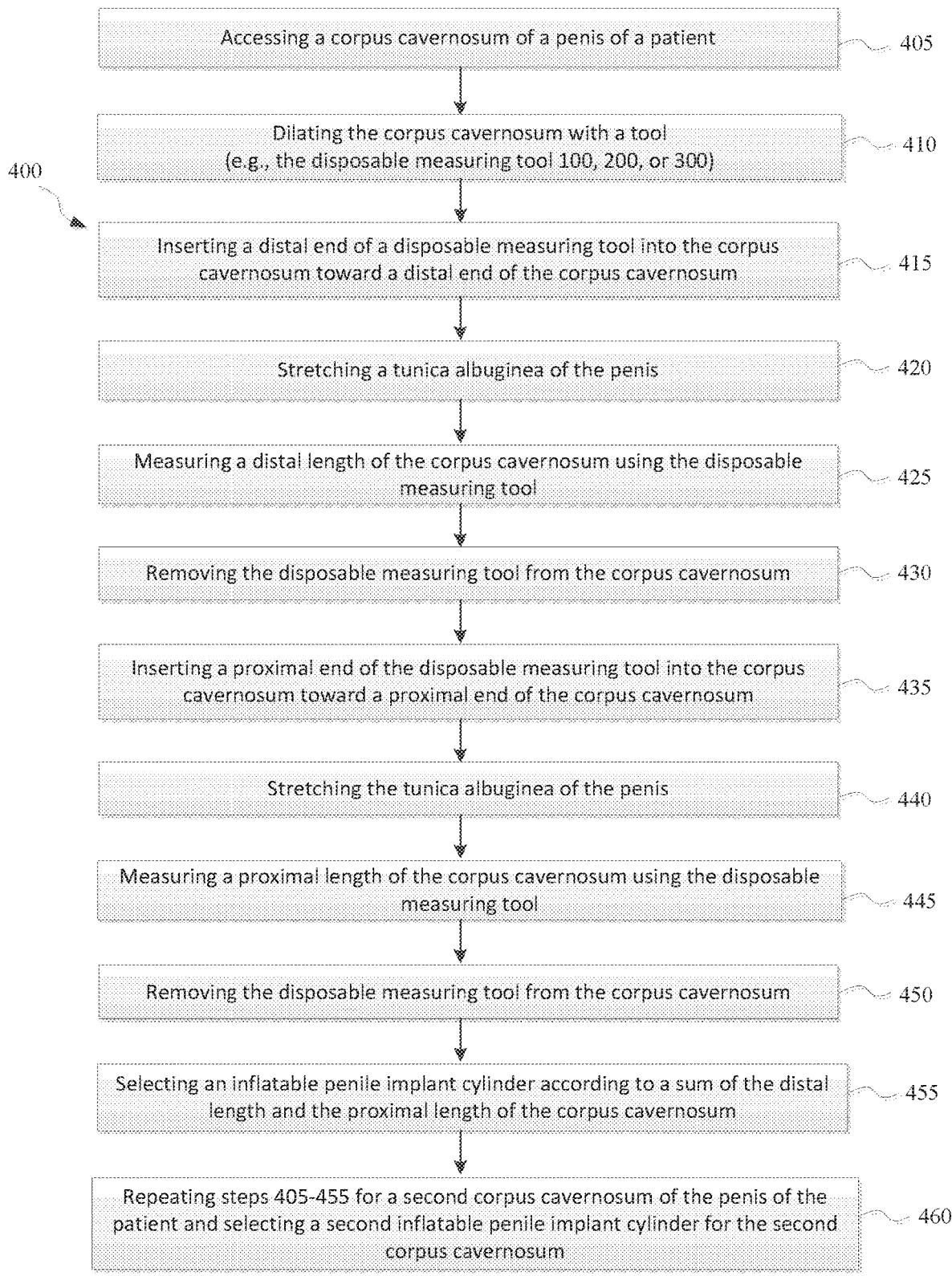
FIG. 4 is a surgical method using a disposable measuring tool according to one embodiment of the disclosure.

FIG. 4 is a surgical method 400 using the disposable measuring tool according to one embodiment of the disclosure. The disposable measuring tool 100 in FIG. 1 can be used in the surgical method 400. The disposable measuring tool 200 in FIG. 2 can be used in the surgical method 400. The disposable measuring tool 300 in FIG. 3 can be used in the surgical method 400.

The method 400 includes 405, accessing a corpus cavernosum of a penis of a patient. In one embodiment, the corpus cavernosum can be accessed through the incision made at the root of the penis.

The method 400 includes 410, dilating the corpus cavernosum with a tool. In one embodiment, the disposable measuring tools 100, 200, 300 can be used to dilate the corpus cavernosum. In other embodiments, instruments such as the Yankauer suction tip, Hegar dilator, Dialmezinsert, and Furlow introducer can be used to dilate the corpus cavernosum.

The method 400 includes 415, inserting a distal end of a disposable measuring tool into the corpus cavernosum toward a distal end of the corpus cavernosum. The distal end of the disposable measuring tool should be configured with the appropriate shape and material to prevent perforation of human tissue. In one embodiment, the distal end of the disposable measuring tool is shaped sufficiently round to prevent perforation. In one embodiment, the distal end of the disposable measuring tool is made with material soft enough to prevent perforation.

The method 400 includes 420, stretching a tunica albuginea of the penis. In one embodiment, the stretching is done gently to mimic an erection. The purpose is to stretch the penis to get an accurate reading of the corpus cavernosum in an erected state.

The method 400 includes 425, measuring a distal length of the corpus cavernosum using the disposable measuring tool. A reading of the distal length of the corpus cavernosum off the "DISTAL" side marking is obtained at this step (see marking examples in FIG. 1).

The method 400 includes 430, removing the disposable measuring tool from the corpus cavernosum.

The method 400 includes 435, inserting a proximal end of the disposable measuring tool into the corpus cavernosum toward a proximal end of the corpus cavernosum. The proximal end of the disposable measuring tool should be configured with the appropriate shape and material to prevent perforation of human tissue. In one embodiment, the proximal end of the disposable measuring tool is shaped sufficiently round to prevent perforation. In one embodiment, the proximal end of the disposable measuring tool is made with material soft enough to prevent perforation.

The method 400 includes 440, stretching the tunica albuginea of the penis. In one embodiment, the stretching is done gently to mimic an erection. The purpose is to stretch the penis to get an accurate reading of the corpus cavernosum in an erected state.

The method 400 includes 445, measuring a proximal length of the corpus cavernosum using the disposable measuring tool. A reading of the proximal length of the corpus cavernosum off the "PROXIMAL" side marking is obtained at this step (see marking examples in FIG. 1).

The method 400 includes 450, removing the disposable measuring tool from the corpus cavernosum.

The method 400 includes 455, selecting an inflatable penile implant cylinder according to a sum of the distal length and the proximal length of the corpus cavernosum.

The method 400 includes 460, repeating steps 405-455 for a second corpus cavernosum of the penis of the patient and selecting a second inflatable penile implant cylinder for the second corpus cavernosum. The selection of the two inflatable penile implant cylinders should be done independently from the other. In some patients, the two corpus cavernosa are in different sizes. Thus, each corpus cavernosum should be measured independently and a matching inflatable penile implant cylinder should be selected independently.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A disposable measuring tool comprising:
   a proximal portion having a proximal diameter; a distal portion having a distal diameter;
   a body portion having a body diameter, wherein the body portion is disposed between the proximal portion and the distal portion, the body diameter is larger than the proximal diameter and the distal diameter;
   wherein each of the proximal portion and the distal portion has a continuous taper where the continuous taper of the proximal portion begins from a midline of the body portion and tapers through the proximal portion to a single rounded proximal end of the disposable measuring tool that is adapted to avoid tissue perforation and the continuous taper of the distal portion begins from the midline of the body portion and tapers through the distal portion to a single rounded distal end of the disposable measuring tool that is adapted to avoid tissue perforation, where an entirety of the disposable measuring tool is located between the proximal end of the disposable measuring tool and the distal end of the disposable measuring tool, and the continuous taper of the disposable measuring tool has a shape adapted to mimic a morphology of a corpus cavernosum of a penis to provide an accurate measurement of a length of the corpus cavernosum of the penis;
   a midline marked along a length of the disposable measuring tool; and
   a measuring surface disposed on the body portion, the measuring surface further including,
   a proximal marking, the proximal marking formed of a first plurality of numeric integers arranged in an upright orientation on a first side of the midline when the proximal end of the disposable measuring tool is inserted into a proximal end of a penis and including first text, on the first side of the midline on the proximal portion and on the distal portion, that indicates the first side of the midline includes the proximal marking; and
   a distal marking, the distal marking formed of a second plurality of numeric integers arranged in an upright orientation on a second side of the midline when the distal end of the disposable measuring tool is inserted into a distal end of the corpus cavernosum of the penis and including second text, on the second side of the midline on the proximal portion and on the distal portion, that indicates the second side of the midline includes the distal marking;
   wherein the second plurality of numeric integers is adjacent to and on an opposite side of the midline relative to the first plurality of numeric integers.

2. The disposable measuring tool according to claim 1, the proximal marking further including
   a third text indicating the proximal end of the disposable measuring tool; and a number indicating a proximal length of the corpus cavernosum.

3. The disposable measuring tool according to claim 1, the distal marking further including
   a fourth text indicating the distal end of the disposable measuring tool; and
   a number indicating a distal length of the corpus cavernosum.

4. The disposable measuring tool according to claim 1, further including
   a proximal length of the proximal portion being about one third of an overall length of the disposable measuring tool;
   a distal length of the distal portion being about one third of the overall length of the disposable measuring tool; and
   a body length of the body portion being about one third of the overall length of the disposable measuring tool.

5. The disposable measuring tool according to claim 1, wherein
   the disposable measuring tool is tapered from a midline of the disposable measuring tool toward both the proximal end of the disposable measuring tool and the distal end of the disposable measuring tool.

6. The disposable measuring tool according to claim 1, further including a malleable mechanism configured to allow the disposable measuring tool to adapt to a shape of the corpus cavernosum.

7. The disposable measuring tool according to claim 1, wherein the proximal portion is continuously tapered from the body portion to the proximal end of the proximal portion such that the proximal diameter of the proximal portion continuously decreases in a direction toward the proximal end.

8. The disposable measuring tool according to claim 1, further comprising:
   a hydrophilic coating applied to the disposable measuring tool.

\* \* \* \* \*

UNITED STATES PATENT AND TRADEMARK OFFICE
CERTIFICATE OF CORRECTION

PATENT NO. : 10,945,638 B2
APPLICATION NO. : 15/298892
DATED : March 16, 2021
INVENTOR(S) : J. Francois Eid It is certified that error appears in the above-identified patent and that said Letters Patent is hereby corrected as shown below:

In the Specification

In Column 4, Line 49, delete "Janerio," and insert -- Janeiro, --, therefor.

In Column 7, Line 38, delete "distal end 110 or proximal end 120." and insert -- proximal end 110 or distal end 120. --, therefor.

In Column 11, Line 4, delete "off" and insert -- of --, therefor.

In Column 11, Line 26, delete "off" and insert -- of --, therefor.

Signed and Sealed this
Thirteenth Day of July, 2021

Drew Hirshfeld
*Performing the Functions and Duties of the*
*Under Secretary of Commerce for Intellectual Property and*
*Director of the United States Patent and Trademark Office*